United States Patent
Agarwal et al.

(10) Patent No.: US 7,088,106 B2
(45) Date of Patent: Aug. 8, 2006

(54) DEVICE AND METHOD FOR THE MEASUREMENT OF GAS PERMEABILITY THROUGH MEMBRANES

(75) Inventors: Pradeep K. Agarwal, deceased, late of Laramie, WY (US); by Rekha Agarwal, legal representative, Laramie, WY (US); John Ackerman, Laramie, WY (US); Ron Borgialli, Laramie, WY (US); Jerry Hamann, Laramie, WY (US); Suresh Muknahalliptna, Laramie, WY (US)

(73) Assignee: University of Wyoming, Laramie, WY (US)

( * ) Notice: Subject to any disclaimer, the term of this patent is extended or adjusted under 35 U.S.C. 154(b) by 0 days.

(21) Appl. No.: 11/022,245

(22) Filed: Dec. 23, 2004

(65) Prior Publication Data

US 2005/0188748 A1    Sep. 1, 2005

(51) Int. Cl.
G01N 27/60  (2006.01)
(52) U.S. Cl. ..................................... 324/455
(58) Field of Classification Search ............... 324/455, 324/464; 73/38
See application file for complete search history.

(56) References Cited

U.S. PATENT DOCUMENTS

| 4,046,843 A | | 9/1977 | Sano et al. |
| 4,360,763 A | * | 11/1982 | Gryzinski ............... 315/111.01 |
| 4,410,338 A | | 10/1983 | Yamamoto et al. |
| 5,062,936 A | | 11/1991 | Beaty et al. |
| 5,863,460 A | * | 1/1999 | Slovacek et al. ...... 252/301.35 |
| 6,245,309 B1 | * | 6/2001 | Etievant et al. ............. 423/248 |
| 6,327,892 B1 | * | 12/2001 | Koiso et al. ................... 73/38 |
| 6,344,133 B1 | * | 2/2002 | Formica et al. ............. 205/775 |

* cited by examiner

*Primary Examiner*—Vincent Q. Nguyen
(74) *Attorney, Agent, or Firm*—Emery L. Tracy

(57) ABSTRACT

A device for the measuring membrane permeability in electrical/electrochemical/photo-electrochemical fields is provided. The device is a permeation cell and a tube mounted within the cell. An electrode is mounted at one end of the tube. A membrane is mounted within the cell wherein a corona is discharged from the electrode in a general direction toward the membrane thereby generating heated hydrogen atoms adjacent the membrane. A method for measuring the effects of temperature and pressure on membrane permeability and selectivity is also provided.

21 Claims, 2 Drawing Sheets

Novel membrane characterization and evaluation cell

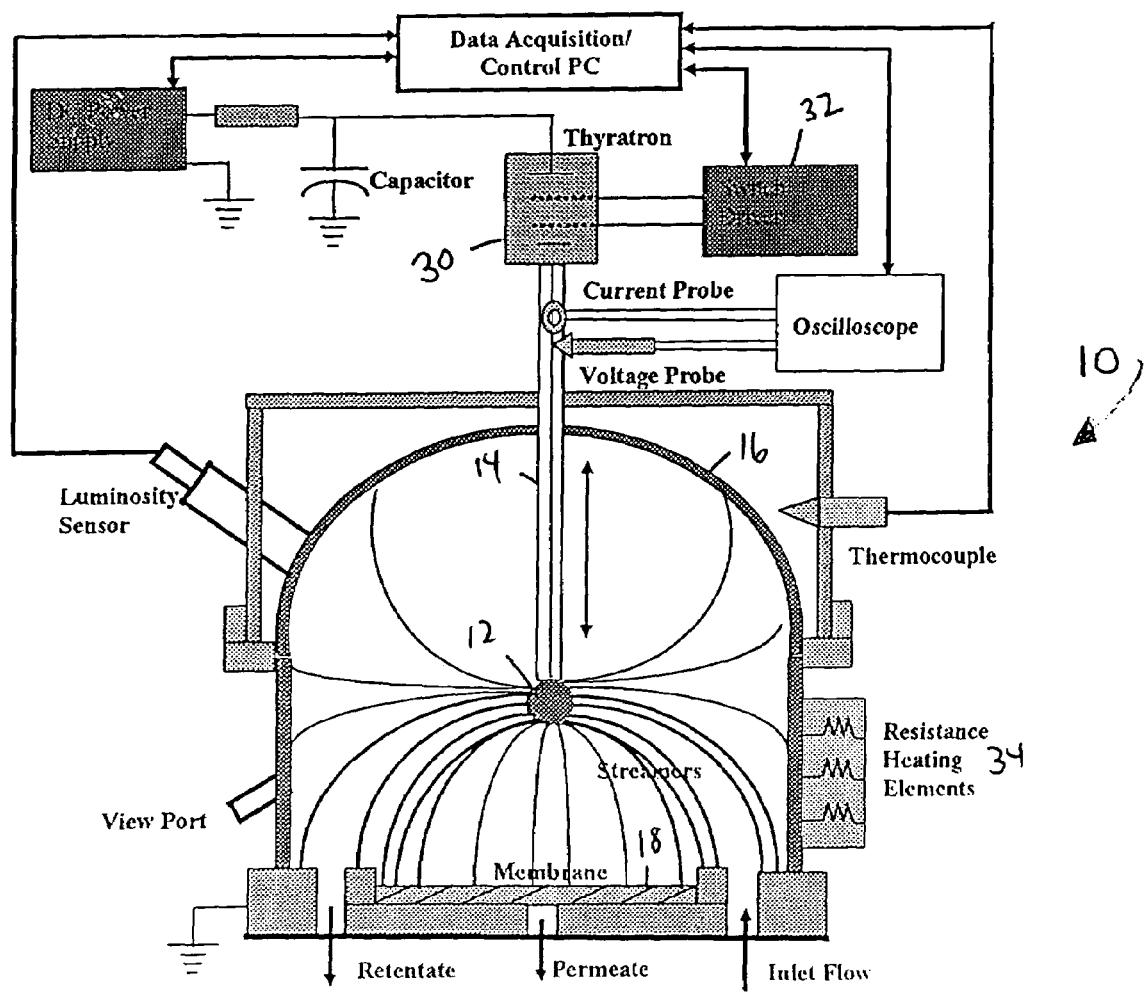
Figure 1: Novel membrane characterization and evaluation cell

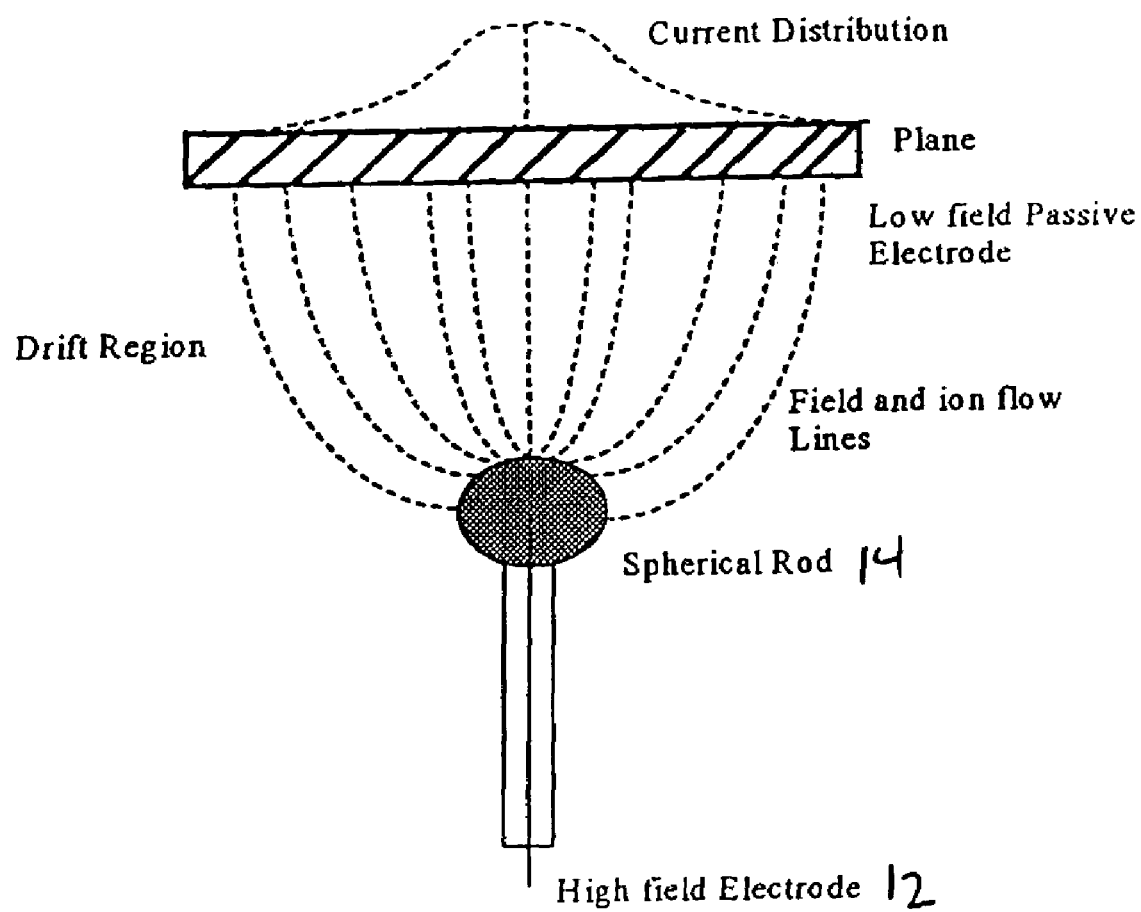
Figure 2: Rod-plane corona: Field and ion flow

DEVICE AND METHOD FOR THE MEASUREMENT OF GAS PERMEABILITY THROUGH MEMBRANES

CONTRACTUAL ORIGIN OF INVENTION

This invention was made with U.S. Government support under Contract No. DE-FC02-91ER75680 awarded by the U.S. Department of Energy. The U.S. Government has certain rights in this invention.

CROSS REFERENCE TO RELATED APPLICATIONS:

This application claims benefit of priority of PCT patent application Ser. No. PCT/US2003/020592, filed Jun. 27, 2003, and U.S. Provisional Application No. 60/392,204 filed Jun. 28, 2002.

BACKGROUND OF THE INVENTION

1. Field of the Invention

Reactant conversion or product yield can often be enhanced by use of membrane reactors that operate on the principle of continuous/intermittent removal of products from the reaction zone. An important category of such reactors is that based on the use of membranes that are selective to the permeation of hydrogen. In the present invention, a device and method is described for the characterization of hydrogen-permeable membranes. This device will, in particular, find application where the permeability of hydrogen has to be measured for membranes to be used in reactors that employ electrical/electrochemical/photo-electrochemical fields that lead to generation of hydrogen.

2. Description of the Prior Art

Many reactions of importance in the process and petroleum industry are limited by thermodynamic constraints on closed system, equilibrium conversion. In such reactions, the reactant conversion can often be enhanced by use of membrane reactors that operate on the principle of continuous/intermittent removal of products from the reaction zone. A particularly important category of such reactors is that based on the use of membranes either, catalytic or non-catalytic, that are selective to the permeation of hydrogen. This configuration, besides overcoming the equilibrium conversion limitations, also provides a relatively pure stream of hydrogen that can be:

recycled to the refinery for use in hydrogenation applications; and/or
used as a clean fuel—in a fuel cell, or in direct combustion applications.

The desire for extraction/separation of hydrogen, in its own right, has long been a goal of the petrochemical industry, as well as those interested in promoting a hydrogen-based energy economy. For example, direct decomposition of hydrogen sulfide to hydrogen and sulfur has been advocated as a valuable source for hydrogen. Conversion, however, is limited by very low reaction rates even at high temperatures. Higher conversions may, at least theoretically, be achieved through use of membrane reactors that remove hydrogen and other products from the reaction zone.

The major obstacle in the development of such systems is the availability of suitable membranes that address to satisfaction the following requirements:

Selectivity for hydrogen;
Permeability to minimize total surface area for the membranes;
Structural/mechanical strength at the operating conditions of interest; and
Economic Value Though many membranes have been proposed, adoption at an industrial scale has been limited. For example, it is known that palladium, and its alloys, can be used as membrane material(s) for generating a very pure stream of hydrogen. However, these membranes lose their catalytic activity, permeability, as well as structural integrity in the presence of even very small quantities of sulfur-containing compounds. This limitation severely restricts application of such membranes in, say, the direct decomposition of hydrogen sulfide, among other applications.

Some have concluded that development in membrane technology was essential for thermal decomposition of hydrogen sulfide to be adopted industrially. Mathematical models confirmed this analysis since the calculated reactor size and performance was found to depend heavily on the diffusion characteristics assumed for the hydrogen-permeable membrane, and the permeate-side flow of sweep gas flow.

In the past few years, a new class of chemical reactors has emerged in which electrical and/or photonic discharges are used to stimulate chemical reactions, for example, $H_2S$ destruction using corona discharges and microwaves. In such reactors, it should also be useful to introduce membranes that enhance conversion, or reduce power input, through removal of continuous/intermittent removal of product(s) from the reaction zone. For example, some have proposed the use of pulsed corona and silent barrier discharge reactors for the decomposition of $H_2S$; the reactor walls, constructed from hydrogen-permeable membrane materials, remove hydrogen from the reaction zone and serve simultaneously as an electrode. High voltage pulses, with duration of about tens of nanoseconds, create an intense electric field in the reaction zone leading to the formation of non-thermal plasma. The temperature of the electrons formed from the ionization of the gaseous medium, as characterized by electron velocity/energy, is much higher than the temperature of the much larger bulk gas molecules and other ionic/charged/excited species leading to a highly efficient process. The major impediment to successful deployment of this non-thermal plasma technology is, once again, the availability of membrane materials that can handle $H_2S$ and successfully remove hydrogen from the reaction zone.

The development of membranes suitable for application in reactors based on the use electrical and/or photonic discharges to stimulate chemical reaction will likely occur. A critical requirement that must be addressed simultaneously is the development of measurement device(s) that can be used to characterize/evaluate membranes in electrical/electrochemical/photo-electrochemical fields. This is essential since hydrogen permeation mechanisms are expected vary markedly in such fields.

In conventional systems, hydrogen molecules must dissociate before they can be adsorbed on the surface of the membrane. These atoms then dissolve in the metal and diffuse, under a concentration gradient, before recombining and degassing on the permeate side of the membrane. At low temperatures, the dissociative adsorption of hydrogen can indeed be the rate-limiting step for the entire permeation process. On the other hand, hot hydrogen atoms created in the plasma region are expected to demonstrate super-permeability or plasma-driven permeation (PDP). Since energy is not required for the dissociative adsorption step, the incorporation of the hydrogen atoms into the membrane material is facilitated greatly. This phenomenon, in fact, may lead to permeabilities higher by several orders of magnitude than conventional membrane systems even at low temperatures, and for surfaces deemed conventionally unclean.

In response to the shortcomings of the art described above, the present invention is described for the characterization of hydrogen-permeable membranes. The device and method of the present invention will, in particular, find application where the permeability of hydrogen must be measured for membranes to be used in reactors that employ electrical/electrochemical/photo-electrochemical fields that lead to generation of hydrogen.

BRIEF DESCRIPTION OF THE DRAWINGS

FIG. 1 is a schematic view illustrating the device and method for the measurement of gas permeability through membranes, constructed in accordance with the present invention, membrane characterization and evaluation cell; and FIG. 2 is a schematic view illustrating the device and method for the measurement of gas permeability through membranes, constructed in accordance with the present invention, with field and ion flow of the rod-plane corona.

SUMMARY

The present invention is a device for the measuring membrane permeability in electrical/electrochemical/photo-electrochemical fields is provided. The device comprises a permeation cell and a tube mounted within the cell. An electrode is mounted at one end of the tube. A membrane is mounted within the cell wherein a corona is discharged from the electrode in a general direction toward the membrane thereby generating heated hydrogen atoms adjacent the membrane.

The present invention further includes a method for measuring the effects of temperature and pressure on membrane permeability and selectivity. The method comprises providing a permeation cell, mounting a tube within the cell, mounting an electrode at one end of the tube, mounting a membrane within the cell, introducing gas into the permeation cell, discharging a corona in a general direction toward the membrane thereby generating heated hydrogen atoms adjacent the membrane, measuring the permeate gas and the retentate gas, and determining the hydrogen flux across the membrane.

DETAILED DESCRIPTION OF THE PREFERRED EMBODIMENTS

As illustrated in FIG. 1, the present invention is a device, indicated generally at 10, for the measurement of membrane permeability in electrical/electrochemical/photo-electrochemical fields. The device 10 includes a high field, spherical electrode 12, mounted at the end of a long glass or ceramic tube 14 and inserted into a dome-shaped permeation cell 16 from the top. The test membrane 18 is mounted at the bottom of the permeation cell 16. The configuration as illustrated herein facilitates a corona discharge, which is a self-sustained electrical discharge in a Laplacian electric field, for the generation of hot hydrogen atoms in the immediate vicinity of the membrane 18.

Typically, a corona discharge consists of high field electrodes or surfaces surrounded by ionization regions producing free charges; low field drift regions in which the free charges drift and react; and low field passive electrodes acting as charge collectors. The three regions are illustrated in FIG. 2 for a typical rod-plane corona test configuration. Under the influence of the local high electric field, and at atmospheric and higher pressures of interest, the breakdown of the gas leads to the formation and transient propagation of streamers characterized by a luminous track of conduction visible to naked eye; the field and ion flow are also shown as dotted lines in FIG. 2.

A pulsed voltage will be applied to the electrodes 12 to facilitate the formation of branched streamers. Note that application of a DC voltage will lead to a straight or axial single streamer corona channel with repetitive streamers traversing the same path. Also, as the repetition rate of the pulsed voltage is increased, the branched streamer coronas will progress towards a single streamer corona. The distance between the spherical electrode 12 and the metallic plate will be varied to increase the intensity and number of streamer coronas as illustrated in FIG. 1.

Traditionally, voltage pulses to generate branched streamer coronas are generated by discharging the energy stored in a capacitance onto the electrode 12 by a spark gap switch. The spark gap switch is usually filled with hydrogen and conduction or breakdown takes place when the voltage across the gap is higher than the gap break down voltage. The gap break down voltage is dependent on the gap distance and pressure under Paschen's Law. The spark gaps tend to have short lifetime of operation and do not provide any control over the initiation of breakdown. In order to overcome these drawbacks, a thyratron switch 30 can be employed. The thyratron switch 30 has a control element known as the grid, which initiates the conduction or breakdown. The grid is driven through a driver circuit 32 controlled by a computer. This can provide precise control of the magnitude of the applied pulse voltage.

A controlled-resistance heating jacket 34 is provided around the permeation cell 16 closer to the membrane 18 to facilitate the investigation of the effect of temperature on membrane permeability.

Various measurement sensors are provided to characterize the permeability of the membrane 18 in terms of input power, and luminosity. Between the spark gap/thyratron switch 30 and the spherical electrode 12, voltage and current sensors are introduced. These sensors, connected to the oscilloscope, facilitate the measurement of the actual electric power injected into the corona discharge region. In addition, the sensors also provide a time-based description of the voltage and current pulses. The luminosity sensor is provided to perform a spectral analysis, if required, of the corona discharge region. A view port is provided to view the streamer corona by the naked eye.

Gas flow into the reactor will depend on the type of measurement required. Metered gas, which is hydrogen in a carrier gas for a membrane permeability test, hydrogen with other gases in a carrier gas for a membrane selectivity test, will be introduced into the test cell as shown in FIG. 2. The permeate and the retentate will be analyzed to determine the hydrogen flux, corrected for pressure, across the membrane 18. The device 10 can then be used to evaluate the effects of:

Pressure;

Temperature; and

Luminosity and input power (related to the production of hot hydrogen atoms) on membrane performance, in terms of permeability and selectivity, for a broad range of operating conditions of interest.

Advantages of the Device

Traditional permeation cells are designed to measure the effects of temperature and pressure on the permeability and selectivity of membranes. In reactors wherein electrical/electrochemical/photo-electrochemical fields are utilized to stimulate chemical reactions, the mechanism of permeation can be substantially different. For example, hydrogen atoms created in plasmas are expected to demonstrate super-permeability even at low temperatures, and for surfaces deemed unclean conventionally. The device 10 of the present invention as illustrated in FIGS. 1 and 2 permits characterization and evaluation of the performance of membranes in such environments. It also permits traditional measurements on the effects of temperature and pressure on membrane permeability and selectivity.

The foregoing exemplary descriptions and the illustrative preferred embodiments of the present invention have been explained in the drawings and described in detail, with varying modifications and alternative embodiments being taught. While the invention has been so shown, described and illustrated, it should be understood by those skilled in the art that equivalent changes in form and detail may be made therein without departing from the true spirit and scope of the invention, and that the scope of the present invention is to be limited only to the claims except as precluded by the prior art. Moreover, the invention as disclosed herein, may be suitably practiced in the absence of the specific elements which are disclosed herein.

What is claimed is:

1. A device for the measuring membrane permeability in electrical/electrochemical/photo-electrochemical fields, the device comprising:
   a permeation cell;
   a tube mounted within the cell;
   an electrode mounted at one end of the tube; and
   a membrane mounted within the cell;
   wherein a corona is discharged from the electrode in a general direction toward the membrane thereby generating heated hydrogen atoms adjacent the membrane such that the permeate through and about the membrane is determined; and
   wherein the corona is a self-sustained electrical discharge in a Laplacian electric field.

2. The device of claim 1 wherein the permeation cell has a substantially dome-shaped configuration having a curved top surface and a substantially planar bottom surface.

3. The device of claim 2 wherein the tube extends through the curved top surface of the permeation cell.

4. The device of claim 1 wherein the membrane is mounted adjacent the bottom surface of the permeation cell.

5. The device of claim 1 wherein the tube is constructed from a material selected from the group consisting of glass and ceramic.

6. The device of claim 1 and further comprising: a pulsed voltage applied to the electrode thereby facilitating formation of branched streamers.

7. The device of claim 1 and further comprising:
   a thyratron switch having a control element driven through a driver circuit controlled by a computer.

8. The device of claim 1 and further comprising:
   a controlled-resistance heating jacket mounted around the permeation cell adjacent the membrane.

9. The device of claim 1 and further comprising:
   measurement sensors for characterizing the permeability of the membrane in terms of input power and luminosity.

10. The device of claim 9 wherein the measurement sensors are voltage, current, and luminosity sensors mounted between the thyratron switch and the electrode.

11. The device of claim 1 and further comprising:
    a view port formed in the permeation cell.

12. A method for measuring the effects of temperature and pressure on membrane permeability and selectivity, the method comprising:
    providing a permeation cell;
    mounting a tube within the cell;
    mounting an electrode at one end of the tube;
    mounting a membrane within the cell;
    introducing gas into the permeation cell;
    discharging a corona in a general direction toward the membrane thereby generating heated hydrogen atoms adjacent the membrane;
    measuring the permeate gas and the retentive gas; and
    determining the hydrogen flux across the membrane.

13. The method of claim 12, and further comprising:
    evaluating the effects of pressure on the membrane performance.

14. The method of claim 12, and further comprising:
    evaluating the effects of temperature on the membrane performance.

15. The method of claim 12, and further comprising:
    evaluating the effects of luminosity and input power on membrane performance in terms of permeability and selectivity.

16. The method of claim 12, and further comprising:
    applying a pulsed voltage to the electrode thereby facilitating formation of branched streamers.

17. The method of claim 12, and further comprising:
    providing a thyratron switch having a control element driven through a driver circuit controlled by a computer.

18. The method of claim 12, and further comprising:
    mounting a controlled-resistance heating jacket around the permeation cell adjacent the membrane.

19. The method of claim 12, and further comprising:
    measuring the permeability of the membrane in terms of input power and luminosity.

20. A device for the measuring membrane permeability in electrical/ electrochemical/photo-electrochemical fields, the device comprising:
    a permeation cell;
    a tube mounted within the cell;
    an electrode mounted at one end of the tube;
    a membrane mounted within the cell; and
    measurement sensors for characterizing the permeability of the membrane in terms of input power and luminosity.
    wherein a corona is discharged from the electrode in a general direction toward the membrane thereby generating heated hydrogen atoms adjacent the membrane such that the permeate through and about the membrane is determined.

21. The device of claim 20 wherein the measurement sensors are voltage, current, and luminosity sensors mounted between the thyratron switch and the electrode.

* * * * *